United States Patent [19]

Beroff et al.

[11] Patent Number: 4,490,326
[45] Date of Patent: Dec. 25, 1984

[54] MOLDING PROCESS FOR POLYDIOXANONE POLYMERS

[75] Inventors: Howard Beroff, Bridgewater; Darrell R. Thompson, Somerville; Robert W. Mericle, Lebanon; William C. Travis, Jr., Bound Brook, all of N.J.

[73] Assignee: Ethicon, Inc., Somerville, N.J.

[21] Appl. No.: 433,177

[22] Filed: Oct. 6, 1982

Related U.S. Application Data

[63] Continuation-in-part of Ser. No. 288,274, Jul. 30, 1981, abandoned.

[51] Int. Cl.$^3$ .......................... B29F 1/06; B29F 1/08; A61B 17/08; A61B 17/12
[52] U.S. Cl. .............................. 264/328.16; 128/325; 128/334 R; 128/346; 264/331.21; 528/354
[58] Field of Search ...................... 264/328.16, 331.21; 528/354; 128/325, 346, 337, 334 R

[56] References Cited

U.S. PATENT DOCUMENTS

| | | | |
|---|---|---|---|
| 2,372,630 | 3/1945 | Smith | 264/328.16 X |
| 3,063,967 | 11/1962 | Schultz | 528/354 |
| 3,063,968 | 11/1962 | Schultz | 528/354 X |
| 3,367,337 | 2/1968 | Javna et al. | 128/325 |
| 3,516,957 | 6/1970 | Gray, Jr. et al. | 264/328.16 X |
| 3,579,751 | 5/1971 | Jonckheere | 128/346 X |
| 3,604,425 | 9/1971 | Le Roy | 128/346 X |
| 3,645,941 | 2/1972 | Snapp et al. | 528/354 X |
| 3,651,203 | 3/1972 | Massonnet | 264/328.16 |
| 3,766,925 | 10/1973 | Rubricius | 128/346 |
| 3,874,042 | 4/1975 | Eddleman et al. | 128/346 X |
| 3,913,586 | 10/1975 | Baumgarten | 128/325 |
| 4,033,938 | 7/1977 | Augurt et al. | 528/354 |
| 4,052,988 | 10/1977 | Doddi et al. | 528/354 X |
| 4,060,089 | 11/1977 | Noiles | 128/325 |
| 4,150,079 | 4/1979 | Chang | 264/328.16 X |
| 4,294,355 | 10/1981 | Jewusiak et al. | 128/325 X |
| 4,317,451 | 3/1982 | Cerwin et al. | 128/325 |
| 4,444,927 | 4/1984 | Borysko | 264/331.21 X |

OTHER PUBLICATIONS

"The Condensed Chemical Dictionary", Eighth Edition, Revised by Gessner G. Hawley, New York, Van Nostrand Reinhold, ©1971, p. 502.

*Primary Examiner*—Philip Anderson
*Attorney, Agent, or Firm*—Robert L. Minier

[57] ABSTRACT

A process for molding surgical clips having improved in vivo performance characteristics from polymers of p-dioxanone. The polymers are heated to a temperature above their melt temperature and the molten polymer injected into a mold maintained at a temperature of 35° C. or less.

11 Claims, 6 Drawing Figures

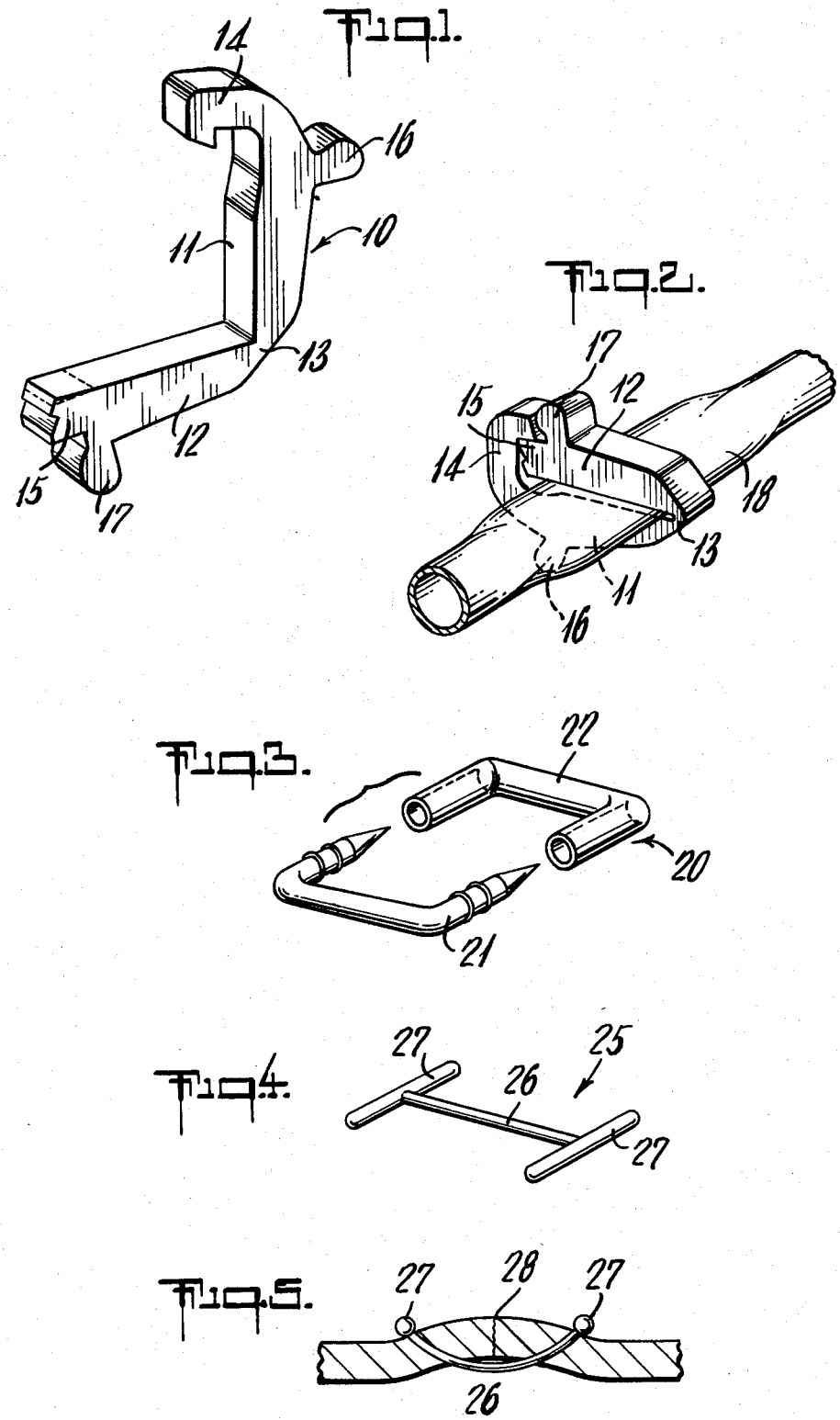

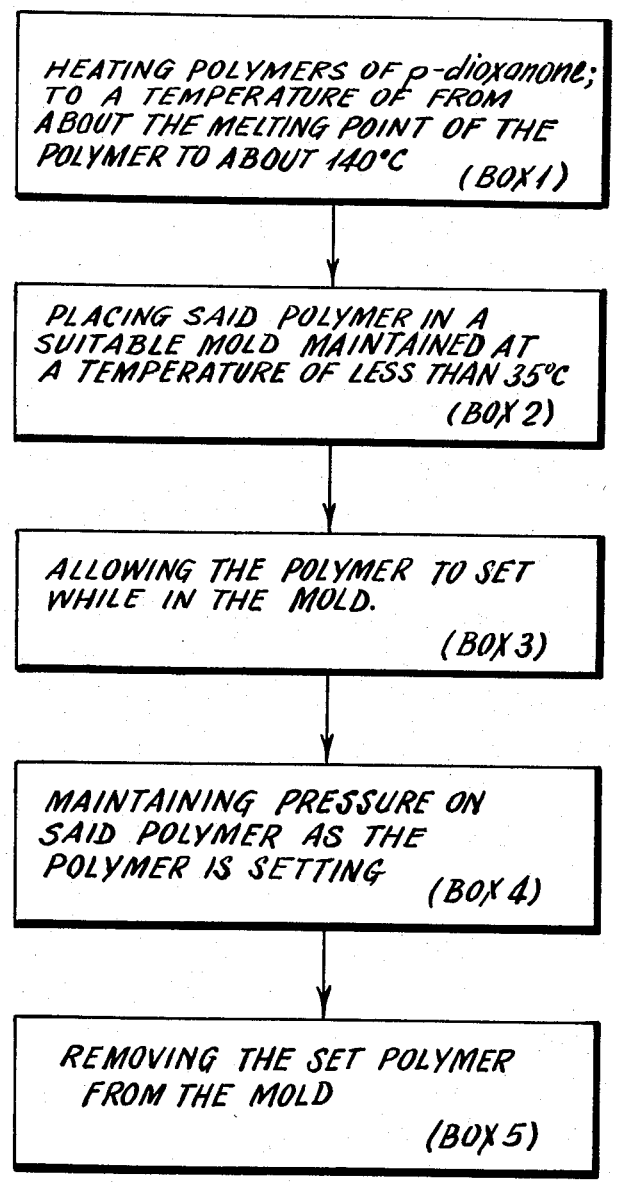

MOLDING PROCESS FOR POLYDIOXANONE POLYMERS

The present application is a continuation-in-part application of patent application Ser. No. 288,274 filed July 30, 1981 now abandoned.

The present invention relates to a process for molding surgical devices and more particularly to molding surgical device from polymers of p-dioxanone, which devices have improved in vivo performance characteristics.

BACKGROUND OF THE INVENTION

It is well known that in many and various surgical procedures, synthetic devices, that is, devices made from foreign materials, are very often used. Examples of such procedures are in surgery wherein tantalum or stainless steel or other metal clips are used to control bleeding by ligating various blood vessels or other tubular organs during surgical procedures. Furthermore, in other surgical procedures, various other metal rods, staples, clips or sheet material are used either to close off fascia or as supports or for other reasons in the surgical procedure. In most instances, these devices remain in the patient for considerable periods of time, though in some instances they may be removed at some later date or even rejected by the natural physiological function of the human body. For the most part, even though these metal surgical devices may cause no harm from the medical viewpoint, it is desired that they not remain in the body as they disrupt postoperative X-ray procedures and the subsequent diagnosis of the patient at times. The metal materials will disrupt X-ray imaging, computerized axial tomography imaging, and other of the new types of diagnostic imaging procedures. Hence, it is desirous that the surgical devices be replaced by non-metallic, biocompatible materials which do not have disruptive effects on the new diagnostic imaging procedures. It is even more desirable in many instances to make the surgical devices from absorbable polymers which will, at an appropriate time, be absorbed by the human body and present no problems whatsoever in future diagnostic imaging procedures. Devices made from absorbable polymers also prevent any long term complication which might arise from having a foreign body present in the tissue.

However, in trying to develop the absorbable polymers to replace the metal materials, it has been found very difficult to obtain an acceptable combination of strength, flexibility and functional integrity in the absorbable polymers. This is especially true in the smaller devices such as ligating clips and other types of clips to either close off vessels or connect material such as tissue. The fine sizes and the small critical areas present in such devices require considerable strength, flexibility and functional integrity. Also the absorbable polymers lack the tactile and audible properties desired in many surgical devices.

One type of absorbable polymer which would be extremely suitable for use in making surgical devices are the polymers of p-dioxanone. These are the polymers that are more fully described in U.S. Pat. No. 4,052,988 issued Oct. 11, 1977, which is incorporated herein by reference. Surgical devices made from the polymers described in the above-mentioned patent would be especially suitable for these surgical devices provided one could make the device from the polymer so that the device had all of the desirable in vivo properties of strength, flexibility, and functional integrity.

SUMMARY OF THE PRESENT INVENTION

What we have discovered is a new and improved process for producing molded surgical devices from polymers of p-dioxanone. The polymers used in our new process are the high molecular weight polymers of p-dioxanone characterized by an inherent viscosity of at least about 0.50 measured as a 0.1% solution in tetrachloroethane at 25° C. and a crystallinity of at least about 20% as determined by X-ray diffraction. Our devices have good flexibility, resiliency, strength, and functional integrity; that is, the devices remain in the positions in which they are placed with minimum creep or movement from that position. The surgical devices produced by our new process have excellent in vivo performance properties in that they maintain their desirable properties for extended periods of time in the patient. The devices produced by our new process maintain a sufficient amount of these desirable properties to accomplish the desired function until the product is substantially absorbed by the physiological function of the human body. Our new process is especially useful when producing small surgical devices of polymers of p-dioxanone such as ligating clips which require a resilient hinge and/or resilient and somewhat flexible latching means, and which devices should maintain their strength and related functional properties for extended periods of time after being implanted in the human body.

In accordance with the present invention, the polydioxanone polymers are first heated to a temperature of from the melting point of polydioxanone (approximately 105° C.) to 140° C. and preferably from about 110° C. to 115° C. The melted polymer is injected in a suitable cavity of a mold. The cavity has the desired shape and size of the desired surgical device. The mold is maintained at a temperature of 35° C. or less and may be as low as 10° C. though we prefer that the mold be maintained at a temperature of about 20° to 30° C. The polymer is allowed to set while in the mold; that is, change from the liquid state it is in when placed in the mold, to a relatively solid state. While the polymer is starting to set and crystallize, it is maintained under pressure. The pressure is sufficient to prevent the polymer from flowing back out of the mold and to allow the crystallization process to begin. After a suitable holding time, the surgical device made from the polymer is removed from the mold. It is preferred that if the surgical device is to be injection molded, at least 50% of the injection pressure be maintained while the device is setting or freezing and that this pressure should be maintained for a time of at least 5 seconds to allow the device to set and start to crystallize in the mold.

DESCRIPTION OF THE DRAWINGS

FIG. 1 is an enlarged perspective view of a ligating clip made from the process of the present invention;

FIG. 2 is an enlarged perspective view showing the clip of FIG. 1 in place closing off a blood vessel;

FIG. 3 is an enlarged perspective view depicting a two-piece fastener made in accordance with the method of the present invention;

FIG. 4 is a perspective view of a wound closure device of the present invention;

FIG. 5 is a cross-sectional view showing the device of FIG. 4 in position to close a wound; and FIG. 6 is a schematic flow diagram showing the various steps in the method of the present invention.

DETAILED DESCRIPTION OF THE EMBODIMENTS OF THE PRESENT INVENTION

The polymers which may be used to make the molded surgical devices in accordance with the method of the present invention are polymers of p-dioxanone. The polymers are comprised of units having the general formula:

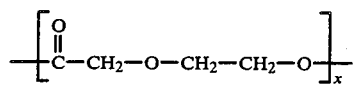

wherein x is the degree of polymerization. The polymer has an inherent viscosity of at least 0.50 measured as a 0.1% solution in tetrachloroethane at 25° C. and a crystallinity of at least about 20% as determined by X-ray diffraction.

These polymers are conveniently prepared from a monomer having the following formula:

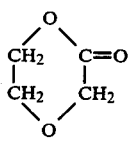

A detailed description of the monomer and polymer and their method of preparation is more fully described in U.S. Pat. No. 4,052,988 issued Oct. 11, 1977.

Referring to the schematic flow sheet FIG. 6, the first step in our new method is to heat the polymer as described to a temperature just above the melting temperature of the polymer (Box 1). We have found suitable temperatures to be from about the melting temperature of polydioxanone or 105° C. to 140° C., with a preferred range for the p-dioxanone polymers being from 110° C. to 115° C. We have found that it is important to keep the temperature as close to the melt point of the polymer as possible in order to obtain the desired in vivo performance from the surgical devices that are molded. The specific apparatus used to melt the polydioxane is not critical to the present invention. We have found that when using reciprocating screw injection molding apparatus fed from a hopper that by heating the barrel electrically we can maintain temperatures in the barrel sufficient to melt the polymer fed into the barrel in pellet form. By maintaining the barrel temperature slightly lower than the melt temperature of the polymer with electrical heat, this electrical heat combined with the heat caused by the shearing forces placed on the polymer by the screw are sufficient to melt the polymer and allow the polymer to be injected by a nozzle into an appropriate mold. It should be noted that other techniques and apparatus for melting polymers and maintaining polymers at desired temperatures may also be used and will depend to a great extent on the specific injection molding machine used and the accessory equipment available. Any well known injection molding apparatus may be used in carrying out our new process; and apparatus include plunger-type molding machines, reciprocating screw machines, injection molding apparatus with separate accumulator devices and the like. This is contrasted to standard techniques where it is desirable to have the polymers relatively fluid and considerably above their melting temperature so that they are fluid and more readily flow into the crevices and corners of the mold and completely fill the mold. The mold may be a single cavity or a multi-cavity mold and any of the standard well known molds may be used. The mold has the desired shape of the surgical device to be manufactured. The mold is maintained at a temperature of 35° C. or less and may be maintained as low as 10° C. (Box 2). We have found that desirable temperatures at which to maintain the mold are from 20° C. to 30° C. Such low mold temperatures are not normally used in the molding of polymers.

Generally, with similar polymers it is desirable to maintain the mold temperature at the temperature which provides the maximum rate of crystallinity in order to decrease cycle times, improve production, and allow the polymer to set at a temperature having a high rate of crystallization to provide strength. The temperature at which the maximum rate of crystallization occurs for polydioxanone has been found to be about 55° C. We have found, unexpectedly, that by using colder temperatures in the mold, we produce ligating clips with unexpectedly improved in vivo performance characteristics.

The polymer is injected into the mold under pressure from about 500 to 1300 pounds per square inch. It is important that a reasonable pressure be maintained on the polymer while it is in the mold until the polymer has had a chance to freeze and set up (Box 3). By "setting" the polymer or having the polymer "set" or "set up" it is meant that the polymer is hardened sufficiently so that it maintains the desired shape. In some instances the polymer may have hardened throughout the shape while in most instances the outer surfaces of the polymer shape has hardened or had a skin formed so that the polymer maintains the desired shape.

We have found that maintaining at least 50% of the initial pressure, that is from about 250 to 650 psi, even as low as 150 psi, may be used to maintain the polymer under pressure during the freezing or setting cycle (Box 4).

The pressure should be maintained on the polymer for about 5 seconds or more to provide the necessary time for the polymer to set and crystallization to start. The resultant molded device may then be removed after a suitable holding time from the mold by standard techniques (Box 5).

One type of surgical device is a ligating clip such as that depicted in FIG. 1. The clip 10 comprises two leg members 11 and 12 connected at their proximal ends by a resilient hinge section 13 and containing at their distal ends 14 and 15 some means of locking the clip in the closed position. Disposed on the outer surfaces are bosses 16 and 17 or other means for use in applying a clip about a vessel. FIG. 2 shows the clip of FIG. 1 in the closed position with the distal ends of the leg members being engaged closing off the lumen of a blood vessel 18.

The following example which is presented by way of illustration is directed primarily to such a ligating clip. It is understood that certain variations that may apply to other surgical devices will be readily apparent to those skilled in the art.

EXAMPLE

Clips, having a configuration as shown in FIG. 1, are produced by injection molding a polydioxanone polymer. A cavity type mold well known in the industry is used to produce the clip. The clips are molded at the various nozzle temperature, (polymer temperature); mold temperatures; and pressures as shown in the following table.

TABLE

| Sample | 1 | 2 | 3 | 4 | 5 | 6 | 7 | 8 | 9 |
|---|---|---|---|---|---|---|---|---|---|
| Test Parameters | | | | | | | | | |
| Barrel/Nozzle Temp. (C.) | 99 | 99 | 100 | 100 | 100 | 120 | 150 | 110 | 115 |
| Mold Temp. (C.) | 15 | 20 | 30 | 35 | 60 | 30 | 30 | 39 | 30 |
| Starting Pressure (psi) | 1250 | 1250 | 1030 | 1100 | 735 | 765 | 660 | 585 | 1175 |
| Retained Pressure (psi) | 1250 | 1250 | 515 | 660 | 440 | 440 | 365 | 0 | 0 |
| Physical Testing | | | | | | | | | |
| Hinge Strength (kg) | 4.27 | 3.66 | 3.73 | 2.44 | 2.13 | 3.17 | 1.95 | 2.40 | 1.73 |
| In Vivo Hinge Strength | | | | | | | | | |
| Baseline (kg) | 3.94 | 3.51 | 3.73 | 2.48 | 2.13 | 3.17 | 1.95 | 2.37 | 1.65 |
| 7 days (kg) | 3.84 | 3.39 | 2.87 | 2.13 | 0.78 | 2.96 | 0.83 | 0.63 | 0.73 |
| % failed at 7 days (no tensile strength) | 0 | 0 | 0 | 0 | 30 | 0 | 45 | 40 | 30 |

The barrel is the cylinder in which the screw is located and the barrel has various temperature zones. The temperature is not necessarily uniform throughout the length of the barrel. The barrel/nozzle temperature is the temperature in the barrel measured in the zone immediately adjacent the nozzle. The actual temperature of the polymer at this point is estimated to be 10° to 15° C. higher than the barrel/nozzle.

The molded clips are tested for various strengths.

The hinge strength of the clip is the force required to break the clip at the hinge area and is determined as follows. The latching mechanism at the distal ends of the conditioned clip is cut away and the cut ends of the leg members placed in the opposite jaws of an Instron Tensiometer. The jaws are steel faced. Using a strain rate of 5 mm/min., the jaws are moved apart and the force necessary to break the hinge is determined in kilograms.

The hinge strength of the clip molded at the various polymer and mold temperatures is provided in the above table.

The clips are also tested for in vivo strength retention properties as described below. Packages containing clips from each submitted lot are opened and the clips removed. The clips are separated without apparent bias into groups consisting of 10 clips each. Each group will correspond to one hinge strength test interval. Special Long Evans rats, weighing 150 to 300 grams, are acclimated for a minimum of one week to surgery. Each rat is prepared for surgery, anesthesized, and 2 clips are implanted in each rat. The clips are implanted in the left and right posterior dorsal subcutis of the rat. At the post implantation, the rats are euthanatized and the clips carefully removed. The hinge strength of the clips is determined by cutting away the latching mechanism at the distal ends of the clip and placing the cut ends of the leg members in the opposing jaws of an Instron Tensiometer. The jaws are steel faced. Using a strain rate of 5 mm/min the jaws are moved apart and the force necessary to break the hinge is determined in kilograms.

As is seen from the above table, clips made at a mold temperature greater than 35° C. do not have the desired in vivo hinge strength. Also, clips made where the polymer is heated to above 140° C. do not have the desired in vivo hinge strength and are not suitable for use in surgical procedures as is also the case with clips made where pressure is not maintained on the clip until it starts to set and crystallize. The clips of the present invention have excellent in vivo hinge strength. The clips maintain their functionality for extended periods of time after being placed in living tissue and in an environment in which they will be ultimately absorbed. This is of critical importance in surgical procedures wherein the clip must perform its desired function and after completing that task be absorbed by the psysiological functions of the body.

Another molded product contemplated by the present invention is a 2-piece fastener, such as shown in FIG. 3. The fastener 20 comprises a staple 21 and a receiver 22 and may be used to secure fascia together or the tissue of internal organs and the like. In FIG. 4, there is shown yet another surgical device 25 for closing a wound. This device comprises a thin rod like member 26 with a bar 27 attached at each end. The device is used to close a wound in the manner depicted in FIG. 5. The bars 27 lie on either side of the wound 28 and the wound itself is spanned by the connecting rod 26. Still other molded products contemplated by the present invention are orthopedic pins, screws, plates and clamps; clips, staples, hooks, buttons and snaps; the various bone substitutes such as mandible prosthesis; needles; intrauterine devices; various tubing and capillaries, such as ureter, cystic duct, etc.; surgical instruments; various vascular implants, couplers or supports; vertebral discs, and the like.

Having now described the present invention, it will be understood by those skilled in the art that variations and modifications of the specific embodiments described above may be employed without departing from the spirit and scope of the invention as defined in the appended claims.

We claim:

1. A method of producing a molded surgical device from polymers having units of the formula:

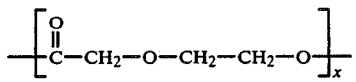

wherein x is the degree of polymerization resulting in a high molecular weight moldable polymer, said polymer having an inherent viscosity of at least 0.50 measured as a 0.1% solution in tetrachloroethane at 25° C. and a crystallinity of at least 20% as determined by X-ray diffraction comprising:
   (a) heating the polymer to a temperature of from about the melt temperature of the polymer to about 140° C.:
   (b) injecting said heated polymer in a mold, said mold being maintained at a temperature of 35° C. or less;
   (c) allowing said polymer to harden sufficient to maintain its shape while in the mold; and
   (d) removing said hardened polymer from the mold.

2. The method according to claim 1 wherein pressure is maintained on the polymer in the mold as the polymer starts to harden and crystallize.

3. The method according to claim 1 or 2 wherein the mold temperature is maintained at from 20° C. to 30° C.

4. The method according to claim 3 wherein the polymer is heated to 110° C. to 115° C.

5. The method according to claim 2 wherein the pressure maintained on the polymer while it is hardening is from about 150 to about 650 pounds per square inch.

6. The method according to claim 2 or 5 wherein the polymer is injected into the mold at a pressure of from about 500 to about 1300 pounds per square inch.

7. The method according to claim 6 wherein at least 50% of the injection pressure is maintained on the polymer while the polymer is hardening.

8. A method for producing a molded ligating clip from a polymer of p-dioxanone, said polymer having an inherent viscosity of at least 0.50 measured as a 0.1% solution in tetrachloroethane at 25° C. and a crystallinity of at least about 20% determined by X-ray diffraction, said clip comprising a pair of leg members connected at their proximal ends by a resilient hinge area and including latching means at the distal ends of said leg members, comprising:
   (a) heating the polymer to a temperature of from about the melt temperature of the polymer to 140° C.;
   (b) injecting said heated polymer under pressure into a mold having the configuration of said ligating clip, said mold being maintained at a temperature of 35° C. or less;
   (c) maintaining pressure on said polymer as the polymer starts to harden and crystallize in the mold;
   (d) allowing the polymer to harden while in the mold; and
   (e) removing said hardened polymer from the mold in the configuration of said ligating clip.

9. The method according to claim 8 wherein the mold temperature is maintained at from 20° C. to 30° C.

10. The method according to claim 8 or 9 wherein the polymer is heated to 110° C. to 115° C.

11. The method according to claim 8 or 9 wherein at least 50% of the injection pressure is maintained on the polymer as it starts to harden and crystallize.

* * * * *

UNITED STATES PATENT AND TRADEMARK OFFICE
CERTIFICATE OF CORRECTION

PATENT NO. : 4,490,326

DATED : December 25, 1984

INVENTOR(S) : Howard Beroff et al.

It is certified that error appears in the above-identified patent and that said Letters Patent is hereby corrected as shown below:

On the title page inventor "William C. Travis" should read

-- Wilson C. Travis --.

Signed and Sealed this

Fourteenth Day of May 1985

[SEAL]

Attest:

DONALD J. QUIGG

Attesting Officer    Acting Commissioner of Patents and Trademarks